(12) United States Patent
Bibette et al.

(10) Patent No.: US 9,604,190 B2
(45) Date of Patent: Mar. 28, 2017

(54) METHOD FOR PREPARING STIFFENED CAPSULES

(71) Applicant: CAPSUM, Marseilles (FR)

(72) Inventors: Jerome Bibette, Paris (FR); Mathieu Goutayer, Saint Malo (FR)

(73) Assignee: CAPSUM, Marseilles (FR)

( * ) Notice: Subject to any disclaimer, the term of this patent is extended or adjusted under 35 U.S.C. 154(b) by 37 days.

(21) Appl. No.: 14/371,656

(22) PCT Filed: Jan. 31, 2013

(86) PCT No.: PCT/EP2013/051931
§ 371 (c)(1),
(2) Date: Jul. 10, 2014

(87) PCT Pub. No.: WO2013/113830
PCT Pub. Date: Aug. 8, 2013

(65) Prior Publication Data
US 2015/0072146 A1 Mar. 12, 2015

(30) Foreign Application Priority Data

Jan. 31, 2012 (FR) .................... 12 50875

(51) Int. Cl.
| | | |
|---|---|---|
| *B01J 13/22* | (2006.01) | |
| *B01J 13/08* | (2006.01) | |
| *B01J 13/10* | (2006.01) | |
| *G01N 33/50* | (2006.01) | |

(52) U.S. Cl.
CPC .............. *B01J 13/22* (2013.01); *B01J 13/08* (2013.01); *B01J 13/10* (2013.01); *G01N 33/5008* (2013.01); *G01N 2500/10* (2013.01); *Y10T 428/2987* (2015.01)

(58) Field of Classification Search
CPC .. A61K 9/5089; A61K 2035/128; A61K 8/11; A61K 9/4816; A61K 9/4891; A61K 49/0091; A61K 49/0093; C08L 5/04; C05G 3/0017; A23L 1/0029; A23L 1/0052; A23L 1/0532; A23L 1/22016; A61L 27/20; B01J 13/08; B01J 13/10; B01J 13/22; G01N 33/5008; G01N 2500/10; Y10T 428/2987
See application file for complete search history.

(56) References Cited

U.S. PATENT DOCUMENTS

| | | | |
|---|---|---|---|
| 5,459,054 A * | 10/1995 | Skjak-Braek | A61K 9/1652 |
| | | | 424/422 |
| 6,982,095 B2 | 1/2006 | Asada et al. | |
| 2003/0175517 A1* | 9/2003 | Voigt | A61K 9/5026 |
| | | | 428/402.2 |
| 2007/0275080 A1* | 11/2007 | Laulicht | B01J 13/08 |
| | | | 424/493 |

FOREIGN PATENT DOCUMENTS

| | | |
|---|---|---|
| CN | 1522113 B | 5/2010 |
| FR | 2955257 A1 | 7/2011 |
| GB | 1399726 | 7/1975 |
| WO | 2009089115 A1 | 7/2009 |
| WO | 2011117727 A1 | 9/2011 |

OTHER PUBLICATIONS

International Search Report mailed Jun. 5, 2013, in International Application No. PCT/EP2013/051931.

* cited by examiner

*Primary Examiner* — Irina S Zemel
(74) *Attorney, Agent, or Firm* — Arrigo, Lee & Guttman LLP

(57) ABSTRACT

The present invention relates to a method for preparing capsules comprising a liquid core, a stiffened intermediate envelope and a gelled external envelope, comprising a step of forming a multi-component liquid drop, a gelification step and a stiffening step.

Figure 1:
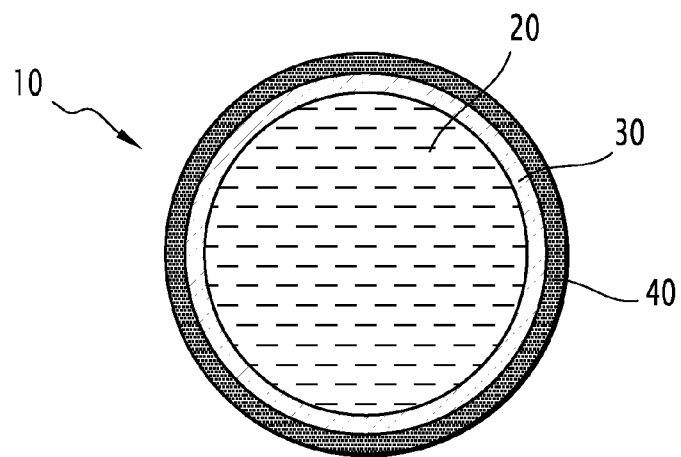

The present invention also relates to a method for preparing capsules comprising a liquid core and a stiffened envelope, comprising a step of forming a multi-component liquid drop, a gelification step, a stiffening step and a depolymerizing step.

12 Claims, 1 Drawing Sheet

METHOD FOR PREPARING STIFFENED CAPSULES

The present invention relates to a method for preparing stiffened capsules, each capsule notably comprising:
- a liquid core comprising an active agent, and
- a stiffened envelope totally encapsulating the liquid core at its periphery.

WO 2010/063937 describes a method for preparing capsules having a gelled outer envelope of small thickness, formed with alginate. These capsules are formed by co-extrusion of drops at the exit of a jacket.

Such a method allows encapsulation in a simple and efficient way of a large variety of liquid products.

Such a method nevertheless has a few limitations depending on the nature of the liquid to be encapsulated. In particular, it is tedious to encapsulate preparations which interact with the liquid containing the liquid polyelectrolytes able to gel. Thus, solutions containing ions such as calcium ions or other divalent ions, of solutions containing a high concentration of alcohol, for example, more than 30% by volume, or further solutions with a pH of less than 4.5 are more difficult to encapsulate by means of the method described in WO 2010/063937.

Moreover, the obtained structures have intrinsic limits faced with certain uses. These limits are set by the properties of the external layers, generally of the hydrogel type. Indeed, a hydrogel layer is very permeable, which may pose a problem when it is sought to encapsulate a species of a molecular size capable of diffusing through the external permeable envelope of hydrogel. The presence of an internal oil layer may participate in increasing the encapsulation properties, but this solution may prove to be insufficient in many practical situations.

An object of the invention is therefore to provide a novel method for preparing capsules, giving the possibility of finding a remedy to these constraints.

An object of the invention is to obtain capsules containing a large variety of liquids and which nevertheless remain easy to form, while having a resistant envelope of small thickness, for ensuring efficient disintegration of the capsule when the liquid contained in the capsule has to be released.

Another object of the invention is to obtain, under mild conditions, resistant capsules having a large variety of surface functions, notably useful in the field of biotechnologies.

An object of the present invention is a method for preparing capsules comprising a step for forming a stiffened envelope around the liquid core of the capsules, intended to meet the encapsulation constraints i.e. avoid any leaking upon storage and allowing sorting out on demand.

This envelope is formed during a stiffening step, during which said envelope is itself protected by a gelled external envelope which has the role of maintaining the multi-layer structure of the capsules before stiffening of the envelope.

Subsequent to the stiffening step, the gelled external envelope may be removed, in order to provide capsules comprising a stiffened external envelope, which may have any type of functionality at their surface.

An object of the present invention is a method for preparing capsules, each capsule comprising a liquid core and a stiffened intermediate envelope totally encapsulating at its periphery, the liquid core, said method comprising the following steps of:
- forming a multi-component liquid drop comprising:
  - a liquid core,
  - a liquid intermediate envelope formed with an intermediate composition comprising at least one first reagent R1, totally encapsulating at its periphery the liquid core, and
  - a liquid external envelope formed with an external aqueous composition, different from the intermediate composition, said composition comprising at least one polyelectrolyte different from the first reagent R1 and at least one surfactant, totally encapsulating at its periphery the intermediate envelope,
- gelling by immersion of said multi-component liquid drop into a gelling solution containing a reagent able to gel the polyelectrolyte of the liquid external envelope, in order to obtain a gelled capsule comprising a gelled external envelope,
- stiffening the first reagent R1 of the liquid intermediate envelope, in order to obtain a gelled and stiffened capsule comprising a stiffened intermediate envelope, and
- recovering said gelled and stiffened capsules.

Within the scope of the present description, by "gelled capsule" is meant a capsule comprising a liquid core and a gelled envelope. Advantageously, a gelled capsule does not comprise any stiffened envelope, but may comprise a liquid intermediate envelope.

Within the scope of the present description, by "gelled and stiffened capsule" is meant a capsule comprising a liquid core, a gelled envelope and a stiffened envelope. Advantageously, the gelled envelope totally encapsulates at its periphery the stiffened envelope, which itself totally encapsulates the liquid core at its periphery.

Through the stiffening step of the method of the invention, the elastic modulus of the intermediate envelope becomes non zero.

Within the scope of the present invention, the liquid intermediate envelope may be stiffened according to any stiffening method which may be contemplated, as for example by polymerization, by precipitation, by colloidal aggregation or else by a glassy transition generally caused by a variation of temperature.

Such capsules, which include a liquid core encapsulated by a substantially solid stiffened envelope, has applications in many technical fields.

In the pharmaceutical industry or in the cosmetic industry, the aforementioned capsules are notably filled with biologically or cosmetically active products. They are notably used for protecting their contents and controlling the sorting out of the product which they contain.

Such capsules are also used in applications in biochemistry for immobilizing cells in bioreactors, or as artificial cells in implants.

The liquid core generally consists of an internal composition, generally liquid or slightly viscous, which may be aqueous or oily. The internal composition may also be a dispersion of water drops in an oily phase, or else a dispersion of oil drops in an aqueous phase, or any other type of multiple emulsion of the water/oil/water type or oil/water/oil type.

The liquid core may optionally comprise suspended solid particles, such as metal nanoparticles, mineral particles or composite particles for example. Advantageously, when they are present, the size of said particles is comprised from 10 nm to 10 µm.

The liquid core generally comprises one or several active agents, selected from cosmetic, pharmaceutical, edible, detergent, or lubricant agents which may be hydrophilic or hydrophobic.

In an alternative, the liquid core comprises a cosmetic active ingredient such as sodium hyaluronate or other moisturizing/repairing molecules, vitamins, enzymes, anti-wrinkle actives, anti-aging agents, protective/anti-radical agents, antioxidants, soothing agents, softening agents, anti-irritation agents, tightening/smoothing agents, emollients, slimming agents, anti-orange peel agents, firming agents, sheathing agents, draining agents, anti-inflammatories, depigmentation agents, whitening agents, self-tanners, exfoliating agents, agents stimulating cell renewal or stimulating skin microcirculation, UV absorbing or filtering agents, anti-dandruff agents.

In another alternative, the liquid core comprises a biological active product advantageously selected from anticoagulants, anti-thrombogenic agents, anti-mitotic agents, anti-proliferation agents, anti-adhesion, anti-migration agents, cell adhesion promoters, growth factors, anti-parasite molecules, anti-inflammatories, angiogenic agents, inhibitors of angiogenesis, vitamins, hormones, proteins, anti-fungal agents, anti-microbial molecules, antiseptics or antibiotics.

The liquid core may also comprise excipients, such as thickeners, or flow property modifying agents. These thickeners are for example polymers, cross-polymers, microgels, gums or proteins, including polysaccharides, celluloses, polyosides, polymers and copolymers based on silicone, colloidal particles (silica, clays, latex . . . ).

Alternatively, the liquid core contains reactive agents such as proteins or reagents intending to form a bioreactor, to form artificial cells for implants, or to encapsulate growing or mature tissues.

Alternatively, the liquid core may contain prokaryotic or eukaryotic cells or organisms. A cosmetic product which may be contained in the liquid core is for example mentioned in Directive 93/35/EEC of the Council dated Jun. 14, 1993. This product is for example a cream, an emulsion, a lotion, a gel or an oil for the skin (hands, face, feet, etc.), a foundation (liquid, slurry), a preparation for baths and showers (salts, foams, oils, gels, etc.), a hair care product (hair and bleaching dyes), a cleansing product (lotions, powders, shampoos), a hair care product (solutions, cleansers, oils), a hair-doing product (lotions, lacquers, brillantine products), a shaving product (soaps, foams, lotions, etc.), a product intended to be applied on lips, a sun-screen product, sunless tanning product, a product for permanently whitening the skin, an anti-wrinkle product.

Edible products able to be consumed by a human being or by an animal are advantageously vegetable or fruit purees such as mango puree, pear puree, coconut puree, cream of onions, leeks, carrots, or other preparations which may mix several fruit or vegetables. Alternatively, these are oils such as a food oil, of the olive oil, soy oil, grapepip oil, sunflower oil type, or of any other oil extracted from plants.

In another alternative, the liquid core may comprise agents intended for detergence purposes, sealants, or coatings, lubrication agents, or else agents intended for the building industry in general.

Within the scope of the present description, by "oily composition" is meant a composition having the property of solubilizing apolar compounds, such as fats, oils or lipids. An oily composition, further said to be hydrophobic, is insoluble in water. Preferably it comprises a fat, an oil or a mixture of plant, animal or mineral origin oils.

As a plant oil, mention may for example be made of sweet almond oil, of jojoba oil, palm oil or phytosqualane.

As fats, mention may for example be made of fatty alcohol and/or fatty acid esters, typically in $C_1$-$C_{20}$, such as isopropyl myristate, glycerol myristate, isononyl isononanoate, caprylic or capric acid triglycerides, isopropyl palmitate and ethyl palmitate. Mention may also be made of silicone oils or polysiloxanes, such as polydimethylsiloxanes (PDMS).

As an animal oil, mention may for example be made of squalene.

As a mineral oil, mention may for example be made of hydrogenated polyisobutylene, isododecane or paraffin oils.

Within the scope of the present invention, by "aqueous composition" is meant a composition having the property of solubilizing polar compounds.

The intermediate envelope is formed with an intermediate composition which may be aqueous or oily. The first reagent R1 of the intermediate envelope may be of the hydrophilic type or of the lipophilic type. The first reagent R1 may be dissolved or else in the form of a dispersion in the intermediate composition. The intermediate composition may notably be a composition comprising a dispersion of particles of the first reagent R1, in an aqueous or oily continuous phase. The intermediate composition is typically a latex of polymers, such as natural latex.

The external envelope is formed with an external aqueous composition and comprises at least one polyelectrolyte which is different from the first reagent R1, and at least one surfactant.

The external aqueous composition is different from the intermediate composition.

The external envelope preferably comprises a reduced amount of surfactant. The mass percentage of surfactants comprised in the external envelope is generally less than or equal to 0.5%, preferably less than or equal to 0.2% and preferentially less than 0.1%, based on the mass of the external envelope.

Within the scope of the present description, by "surfactant" is meant an amphiphilic molecule having two portions with different polarity, one lipophilic and apolar, the other one hydrophilic and polar. A surfactant may be of the ionic type (cationic or anionic), zwitterionic or non-ionic.

Within the scope of the present description, by "multi-component drop" is meant a liquid drop consisting of a liquid central core, of a liquid intermediate envelope, totally encapsulating at its periphery the liquid core, and of a liquid external envelope totally encapsulating at its periphery the liquid intermediate envelope.

The intermediate envelope is in contact with the core and the external envelope and maintains the core out of contact with the external envelope.

Production of Multi-Component Drops

The production of this type of drop is generally carried out by co-extrusion of the various compositions, i.e. the internal composition, the intermediate composition and the external aqueous composition as defined in the aforementioned method.

According to an embodiment, the internal composition is aqueous and the intermediate composition is oily.

According to another embodiment, the internal composition is oily and the intermediate composition is aqueous.

According to another embodiment, the internal composition is aqueous and the intermediate composition is aqueous.

Production of multicomponent drops by co-extrusion may be accomplished for example by separate conveyance in a triple envelope of three flows: a first flow consisting of the internal composition, a second flow consisting of intermediate composition, and a third flow consisting of the external aqueous composition, as described in application FR 1061404.

At the exit of the triple envelope, the three flows come into contact and then a multicomponent drop is formed, according to a hydrodynamic method said to be a "dripping" method (dropwise, notably as described in WO 2010/063937) or a "jetting" method (formation of a liquid jet at the exit of the triple envelope, notably as described in FR 1056925). The first flow forms a liquid core, the second flow forms the liquid intermediate envelope and the third flow forms the liquid external envelope.

According to the production method, each multicomponent drop detaches from the triple envelope and falls into a volume of air, before being immersed into a gelling solution S1 containing a reagent able to gel the polyelectrolyte of the liquid external envelope, in order to form the gelled external envelope of the capsules according to the invention.

According to certain alternatives, the multicomponent drops may comprise additional layers between the external case and the liquid core, other than the intermediate envelope. This type of drop may be prepared by a separate conveyance of multiple compositions in devices with multiple envelopes.

Gelling Step

When the multi-component drop comes into contact with the gelling solution, the reagent able to gel the polyelectrolyte present in the gelling solution then forms bonds with the various chains of polyelectrolyte present in the liquid external envelope, then passes to the gelled state, thereby causing gelling of the liquid external envelope.

Without intending to be bound to any particular theory, when the polyelectrolyte passes to the gelled stated, the individual polyelectrolyte chains present in the liquid external envelope connect with each other so as to form a cross-linked network, also called a hydrogel.

Within the scope of the present description, the polyelectrolyte present in the gelled external envelope is in the gelled state and is also called a polyelectrolyte in a gelled state or further a gelled polyelectrolyte.

A gelled external envelope, able to retain the assembly formed by the core and the intermediate envelope is thereby formed. This gelled external envelope has a specific mechanical strength, i.e. it is capable of totally surrounding the intermediate envelope and of retaining the core encapsulated by this intermediate envelope. This has the effect of maintaining the internal structure of the liquid core and of the intermediate envelope.

Generally, the gelled external envelope appears in the form of a monolayer envelope, totally encapsulating the liquid intermediate envelope at its periphery.

The capsules according to the invention dwell in the gelling solution for the time during which the external envelope is completely gelled.

The gelled capsules may then be optionally collected and immersed in an aqueous rinsing solution, generally essentially consisting of water, in order to rinse the formed gelled capsules. This rinsing step gives the possibility of extracting from the gelled external envelope a possible excess of reagents able to gel from the gelling solution, and all or part of the surfactant (or other species) initially contained in the external aqueous composition.

The presence of a surfactant in the external aqueous composition allows improvement in the formation and gelling of the multi-component drops according to the method as described earlier.

The polyelectrolyte of the gelled external envelope of the capsule according to the invention is advantageously selected from polyelectrolytes which react to multivalent ions.

Within the scope of the present invention, by "polyelectrolyte which reacts to multivalent ions" is meant a polyelectrolyte capable of passing from a liquid state in an aqueous solution to a gelled state under the effect of contact with a gelling solution containing multivalent ions, such as ions of an earth alkaline metal for example selected from calcium, barium or magnesium ions.

In a liquid state, the individual polyelectrolyte chains are substantially free to flow relatively to each other. A 2% polyelectrolyte aqueous solution by mass then has a purely viscous behavior at the characteristic shearing gradients of the shaping method. The viscosity of this zero shearing solution is between 50 mPa·s and 10,000 mPa·s, advantageously between 3,000 mPa·s and 7,000 mPa·s.

The individual polyelectrolyte chains in the liquid state advantageously have a molar mass of more than 65,000 g/moles.

Said gelling solution S1 is for example an aqueous solution of a salt of the type $X_nM_m$ wherein X is for example a halide ion such as a chloride, bromide, iodide or fluoride ion, or further a tartarate ion, and M is advantageously a multivalent cation of an earth alkaline element such as calcium, magnesium or barium and n and m are greater than or equal to 1.

The concentration of a salt of the $X_nM_m$ type in the gelling solution is advantageously comprised from 5% to 20% by mass.

In the gelled state, the individual polyelectrolyte chains form with the multivalent ions, a coherent three-dimensional network which retains the core and the intermediate envelope and prevents its flowing. The individual chains are retained relatively to each other and cannot freely flow relatively to each other. Further, the gel has a yield stress threshold. This yield stress threshold is greater than 0.05 Pa. The gel also has a non-zero elasticity modulus and greater than 35 kPa.

The polyelectrolyte is preferably harmless for the human body. For example, it is produced biologically.

Advantageously, it is selected from polysaccharides, synthetic polyelectrolytes based on acrylates (sodium, lithium, potassium or ammonium polyacrylates or polyacrylamide), or synthetic polyelectrolytes based on sulfonates (sodium, poly(styrene sulfonate), for example).

Preferably, the polyelectrolyte is selected from food polysaccharides which react to multivalent ions.

More particularly, the polyelectrolyte is selected from alkaline alginates, such as sodium alginate or potassium alginate, gellans and pectins.

In the case when the polyelectrolyte is sodium alginate (NaAlg) and when the reagent is calcium chloride, the reaction which occurs during gelling is the following:

$$2\text{NaAlg} + \text{CaCl}_2 \rightarrow \text{Ca(Alg)}_2 + 2\text{NaCl}$$

The alginates are produced from brown algae called "kelps", also designated as "sea weed".

Preferably, the polyelectrolyte is an alkaline alginate advantageously having a block α-L-guluronate content of more than 50%, notably of more than 55%, or even more than 60%.

The polyelectrolyte is for example a sodium alginate.

According to a preferred embodiment, the total mass percentage of polyelectrolytes in the gelled external phase is comprised from 0.5% to 5%, preferably less than 3%.

The total mass polyelectrolyte percentage in the gelled external phase, is for example equal to 2%.

Stiffening Step

The gelled capsules obtained at the end of the gelling step, optionally rinsed, are then subject to a stiffening step of the first reagent R1.

As a first reagent R1, it is possible to use a polymer or a mixture of polymers optionally present in the form of a colloidal dispersion. It is also possible to use a monomer or a mixture of monomers.

In order to carry out this step, the gelled capsules are generally immersed in a stiffening bath.

According to a first embodiment, the stiffening bath corresponds to the gelling solution used during the gelling step. Advantageously, the capsules are gelled and then stiffened in the gelling solution.

According to another alternative, the stiffening bath is different from the gelling solution and it is therefore generally necessary to collect the gelled capsules, optionally rinse them, and then immerse them in the stiffening bath for carrying out the stiffening step.

The stiffening step is typically carried out by coacervation of the first reagent R1 of the liquid intermediate envelope.

Stiffening, notably by coacervation, is achieved in the presence of the external envelope and through the latter after its gelling. The external envelope therefore plays a role of an external mold while producing the stiffened intermediate envelope.

According to this embodiment, the coacervation of the first reagent R1 contained in the intermediate envelope, causes stiffening of said liquid envelope, which has the advantage of giving superior mechanical strength to said capsules.

Within a coacervate comprising a first reagent R1 of the polymer type, the bonds binding the polymer chains with each other are generally of the ionic type and are generally stronger than the bonds present within a membrane of the surfactant type.

Several coacervation methods for the first reagent R1 may be used.

According to a first embodiment, the coacervation of the first reagent R1 is caused by a variation of the temperature or of the pH, or by electromagnetic radiation.

According to this embodiment, the stiffening bath generally does not comprise any stiffening agent, but induces coacervation by varying the reaction conditions, which may correspond to a variation in the temperature, in the pH or in the concentration or dilution conditions, or to the application of UV or IR radiation preferably by a variation of the temperature.

A first reagent R1 adapted to this first embodiment may be selected from biopolymers of the protein type, such as those intended for forming extracellular biological matrices. As a bio polymer adapted to the invention, mention may be made of Matrigel™ for example, which is liquid at a low temperature and becomes elastic at room temperature, or else collagen which gels at low temperature. Alternatively, the gelling kinetics of a collagen solution are increased by neutralization of the pH. Indeed, collagen is soluble in an acid aqueous solution, generally of acetic acid, and neutralization of the pH gives the possibility of regenerating electrostatic interactions between the filaments of collagen in order to form structured fibers within a lattice. The collagen thus forms a gel when its pH is neutralized.

This first embodiment is particularly suitable for the field of biotechnologies.

According to another embodiment, the coacervation of the first reagent R1 is carried out by coacervation with a multivalent cation.

According to a first alternative, the multivalent cations are contained in the stiffening bath (or optionally in the gelling solution) and diffused through the gelled external envelope for reacting with the first reagent R1 and forming a coacervate.

The hydrogel forming the gelled external envelope is generally sufficiently permeable for allowing permeation of multivalent cations.

As a first reagent R1 adapted to this first alternative, mention may for example be made of a hydrophilic polyelectrolyte, more particularly a polysaccharide (however different from the polyelectrolyte of the gelled external envelope).

As a first reagent R1 also adapted to this first alternative, mention may be made of natural latex, in the form of a colloidal dispersion of polymers. A multivalent cation adapted to this embodiment is for example, a cation of an earth alkaline element such as calcium, magnesium or barium.

According to another embodiment, the coacervation of the first reagent R1 is carried out by coacervation with a second reagent R2, different from the first reagent R1.

According to a first alternative, the second reagent R2 is contained in the stiffening bath (or optionally in the gelling solution) and diffuses through the gelled external envelope in order to react with the first reagent R1 and form a coacervate.

The hydrogel making up the gelled external envelope is generally sufficiently permeable for allowing permeation of such polymers.

According to another alternative, the second polymer P2 is contained in the intermediate composition forming the liquid intermediate envelope even before immersion in the stiffening bath, and, during the immersion in the stiffening bath, a change in the conditions of temperature or of pH causes coacervation of the first reagent R1 with said second reagent R2.

The formation of the coacervate between both reagents R1 and R2 is generally caused by a variation in the conditions of the reaction medium (temperature, pH, reagent concentration, etc.), generally caused by immersion into the stiffening bath.

Typically, the first reagent R1 and the second reagent R2 are charged polymers with opposite charges.

In this case, the coacervation reaction results from the neutralization of both of these charged reagents R1 and R2 of opposite polarities, and allows the formation of a stiffened membrane structure by electrostatic interactions between the reagents R1 and R2. The stiffened intermediate envelope thereby formed around each core, encapsulates it totally and isolates it from the outside, and notably from the gelled external envelope.

Preferably, the first reagent R1 is a charged polymer (or polyelectrolyte of the anionic or cationic type).

Preferably, the second reagent R2 is a charged polymer (or polyelectrolyte) of charge opposite to the first reagent R1, of the cationic or anionic type, preferably hydrophilic.

According to other alternatives, the first reagent R1 is a mixture of charged polymers with the same polarity.

According to other alternatives, the second reagent R2 is a mixture of charged polymers of the same polarity, but with a polarity opposite to that of the first reagent R1.

According to another embodiment, the first reagent R1 is a monomer or a mixture of monomers, able to polymerize with the second reagent R2, in the form of a polymer or monomer, optionally in the presence of a polymerization agent.

Said second reagent R2 may be present in the stiffening bath and may pass through the permeable gelled external envelope for polymerizing with the first reagent R1.

Alternatively, the second reagent R2 may be present in the intermediate composition, and polarization is caused by permeation of a polymerization agent, contained in the stiffening bath.

In both of these cases the coacervation of the intermediate envelope is due to the polymerization of both reagents R1 and R2.

As reagents R1 and R2, mention may for example be made of monomers able to form coacervates of polyurethanes, such as polyisocyanates and polyols, or further monomers able to form polyacrylamide coacervates.

According to a first alternative, the first reagent R1 is a hydrophilic anionic polymer and the second reagent R2 is a hydrophilic cationic polymer.

According to this alternative, the intermediate composition comprising the first anionic, hydrophilic reagent R1 is an aqueous composition.

According to this alternative, the second cationic hydrophilic reagent R2 may be contained in an aqueous stiffening bath or in the aqueous intermediate composition.

As a first reagent R1 adapted to this alternative, mention may for example be made of polyacrylic acid, polysaccharides.

As a second reagent R2 adapted to this alternative, mention may for example be made of gelatin, chitosan.

According to another alternative, the first reagent R1 is a hydrophilic cationic polymer and the second reagent R2 is a hydrophilic anionic polymer.

According to this alternative, the intermediate composition comprising the first hydrophilic cationic reagent R1 is an aqueous composition.

According to this alternative, the second hydrophilic anionic reagent R2 may be contained in an aqueous stiffening bath or else in the aqueous intermediate composition.

As a first reagent R1 adapted to this alternative, mention may for example be made of gelatin, chitosan.

As a second reagent R2 adapted to this alternative, mention may for example be made of polyacrylic acid, polysaccharides.

According to another alternative, the first reagent R1 is a lipophilic cationic polymer and the second reagent R2 is a hydrophilic anionic polymer.

According to this alternative, the intermediate composition comprising the first lipophilic cationic reagent R1 is an oily composition.

According to this alternative, the second lipophilic anionic reagent R2 is contained in an oily stiffening bath.

As a first reagent R1 adapted to this alternative, mention may for example be made of aminosilicone.

As a second reagent R2 adapted to this alternative, mention may for example be made of polyacrylic acid, polysaccharides.

Within the scope of the following description by "polymer of the anionic type" or "anionic polymer" is meant a polymer including chemical functions of the anionic type. They may also be referred to as an anionic polyelectrolyte.

By "chemical function of the anionic type", is meant a chemical function AH capable of yielding a proton for obtaining a function A-. According to the conditions of the medium in which it is found, the polymer of the anionic type therefore includes chemical functions in the form of AH, or else in the form of its conjugate base, A-.

As an example of chemical functions of the anionic type, mention may be made of the carboxylic acid —COOH versions, possibly present in the form of an carboxylate anion —COO—.

As an example of a polymer of the anionic type, mention may be made of any polymer stemming from the polymerization of monomer units including at least one chemical function of the carboxylic acid type. Such monomers are for example, acrylic acid, maleic acid or any ethylenically unsaturated monomer including at least one carboxylic acid function.

Among the examples of polymer of the anionic type suitable for applying the invention, mention may be made of copolymers of acrylic acid or maleic acid and of other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxyester acrylates.

Within the scope of the present description, by "polymer of the cationic type" or "cationic polymer" is meant a polymer including chemical functions of the cationic type. They may also be referred to as cationic polyelectrolyte.

By "chemical function of the cationic type", is meant a chemical function B capable of capturing a proton in order to obtain a $BH^+$ function. Depending on the conditions of the medium in which it is found, the polymer of the cationic type therefore includes chemical functions in the form of B or else in the form of $BH^+$, its conjugate acid.

As an example of chemical functions of the cationic type, mention may be made of primary, secondary and tertiary amine functions optionally present in the form of ammonium cations.

These functions may be comprised within the main chain of the cationic polymers or else be borne by said chain or else borne by side chains.

As an example of a polymer of the cationic type, mention may be made of any polymer stemming from the polymerization of monomer units including at least one chemical function of the primary, secondary or tertiary amine type. Such monomers are for example, monomers including aziridine functions or any ethylenically unsaturated monomer including at least one primary, secondary or tertiary amine function.

Among the examples of polymer of the cationic type, suitable for the application of the invention, mention may be made of silicone polymers modified with primary, secondary or tertiary amine functions, such as amodimethicone, derived from a silicon polymer (polydimethysiloxane, also called dimethicone):

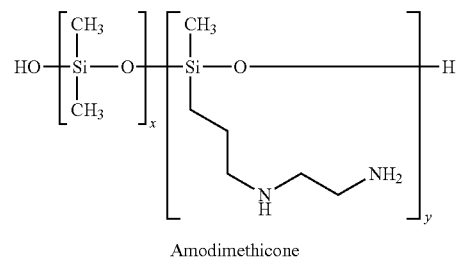

Amodimethicone

Mention may also be made of derivatives of amodimethicone, such as for example copolymers of amodimethicone, aminopropyl dimethicone, and more generally silicone polymers including amine functions.

Mention may be made of the copolymer of bis-isobutyl PEG-14/amodimethicone and bis hydroxy/methoxy amodimethicone.

Mention may also be made of polymers of the polysaccharide type comprising amine functions, such as chitosan.

Mention may also be made of polymers of the polypeptide type comprising amine functions, such as polylysine.

Mention may also be made of polymers of the polyethylene imine type comprising amine functions, such as linear or branched polyethyleneimene.

Preferably, the first reagent R1, and optionally the second reagent R2 when it is present, is in the form of a latex of polymers.

Within the scope of the present invention, by "latex" is meant a stable aqueous dispersion of particles of polymers, generally with a size comprised between 100 nm and 10 μm, preferably between 100 nm and 1 μm, or further between 1 μm and 10 μm.

Natural latex dispersions are available commercially and may be diluted before use in order to reduce their mass fraction of particles of polymers. Generally, within the scope of the present invention, natural latex dispersions are used with a mass fraction comprised between 10% to 60%, preferably from 20% to 40%.

A polymer latex composition may be stiffened by migration, through the gelled envelope, of calcium ions contained in the stiffening bath.

In the case of a natural latex the latter is transformed into rubber during the stiffening step.

The intermediate composition comprising the first reagent R1, may further comprise a filling agent, notably when the first reagent R1 is in the form of a polymer latex.

This filler gives the possibility of reinforcing the stiffness and the resistance of the stiffened intermediate envelope.

As suitable fillers, mention may be made of silica, carbon black, and generally any inorganic compound in the form of colloidal particles.

An object of the present invention is also a method for preparing capsules as described earlier, and further comprising after the stiffening step, a step for depolymerization of the polyelectrolyte in the gelled state of the gelled external envelope, in order to remove the gelled external envelope.

Depolymerization Step

The depolymerization step has the purpose of suppressing the gelled external envelope without altering the structure of the stiffened intermediate envelope.

This step may be carried out with any method for depolymerizing the hydrogel formed during the gelling step. In the case of a gelled external envelope of alginate, depolymerization may be carried out by immersion in a depolymerization solution, such as for example a sodium citrate solution concentrated to a mass content of a minimum of 5%, typically 10%, or else a saline phosphate buffer solution (further called a PBS buffer).

Mention may further be made of solutions of tartrate ions, of phytic acid or of EDTA, any solution of so-called chelating species for divalent cations, or further solutions of polymers of acrylic acid of the carbomer, carbopol, polyacrylamide or polyacrylate type.

Generally, the stiffened intermediate envelope is not altered by the step for depolymerizing the gelled external envelope.

An object of the present invention is also capsules comprising a liquid core and a stiffened envelope totally encapsulating at its periphery the liquid core, which may be obtained according to one of the methods described above.

According to one embodiment, the capsules may further comprise a gelled external envelope totally encapsulating at its periphery the stiffened envelope.

Such capsules correspond to the gelled and stiffened capsules defined above, and are typically obtained at the end of the stiffening step of the method of the invention.

According to another embodiment, the capsules consist of a liquid core and of a stiffened external envelope totally encapsulating at its periphery the liquid core.

Such capsules correspond to stiffened capsules without any gelled envelope. These capsules are typically obtained at the end of the depolymerization step of the method of the invention.

After removing the gelled external envelope, the stiffened intermediate envelope becomes the stiffened external envelope of the stiffened capsules. These capsules then benefit from the surface properties of the stiffened envelope, which may be of a hydrophilic type or of the lipophilic type.

The stiffened envelope is intended to provide new surface properties to the capsules of the core/envelope type described earlier, by getting rid of the limits set by the nature of the external envelope, which was up to now essentially of the hydrogel type (cf. notably WO 2010/063937).

Given the diversity in the selection of the materials forming the stiffened intermediate envelope, the thereby obtained capsules may have any type of functionality at their surface.

It is therefore possible to concentrate the preparation of capsules having surface properties adapted to various fields, such as for example in biotechnology applications.

It is therefore also possible to contemplate the obtaining of highly superior encapsulation performances without any constraints on the nature of the solution to be encapsulated. This is particularly sought in certain applications for which there are no existing satisfactory solutions.

As an example of surface properties of interest which were not available with known capsules including a gelled envelope up to now, and which are accessible from now on with the stiffened capsules according to the invention, mention may be made of sealing, stiffness or, on the contrary, elasticity properties or further having biomimetism properties.

In particular, when the stiffened envelope is based on latex, stiffened capsules are obtained, including an external envelope with a great seal, even towards water.

In particular, when the stiffened envelope is based on biopolymers of a protein type, such as Matrigel™ or collagen, stiffened capsules are obtained including a envelope for which the internal surface is biomimetic and favorable for the growth of plant, animal, or human cells.

Preferentially, the stiffened envelope is formed with a mixture of a biopolymer and of a polyelectrolyte. For example, the stiffened envelope is a mixture of collagen and alginate. The biopolymer/polyelectrolyte volume is typically greater than 75/25, preferably comprised from 75/25 to 99.9/0.1; 80/20 to 90/10; 70/30 to 80/20; 65/35 to 75/25.

Generally, a stiffened envelope for example obtained by coacervation of polymers is stiffer, more impervious and less permeable than a gelled envelope obtained by gelling.

Therefore, it is understood that the stiffened capsules of the invention have increased imperviousness properties as compared with simply gelled capsules of the prior art.

It is also possible to functionalize the surface of the stiffened envelope in order to provide the capsules with the desired properties, such as hydrophilicity, lipophilicity, electric charge properties.

Encapsulation, as an active agent, of cosmetic, pharmaceutical, edible compounds, lubricants, proteins, reagents intended to form a bioreactor or cells intended to divide may notably be contemplated.

It is also possible to contemplate the encapsulation of cells for implants or cells intending to form tissues, such as spontaneous assemblies of cells during division. In this case, the different external envelope of the capsules is advantageously permeable to the nutrients of the outer legion so that the tissues develop efficiently.

It is also possible to contemplate the encapsulation of detergents and/or enzymes for liquid detergents. In this case, the stiffened external envelope of the capsules, typically based on latex, is advantageously permeable only to water. The salting out of the core is then typically caused by bursting of the capsule with an osmotic shock when the capsule comes into contact with water.

Characteristics of the Gelled and Stiffened Capsules

Preferably, the gelled external envelope of the capsule according to the invention has a thickness comprised from 10 μm to 500 μm, preferably from 20 μm to 200 μm and advantageously from 50 μm to 100 μm.

The fineness of the thickness of the gelled external envelope generally gives the possibility of making this external envelope transparent.

The capsules according to the invention generally have a volume ratio between the core and the whole of the intermediate and external envelopes of more than 2, and preferably less than 50.

According to a particular embodiment, the capsules according to the invention generally have a volume ratio between the core and the whole of the intermediate and external envelopes comprised between 5 and 10.

The mass percentage of surfactant comprised in a capsule according to the invention is generally less than or equal to 0.050%, preferably less than or equal to 0.025% and preferentially less than or equal to 0.010%, or even less than or equal to 0.005%, based on the total mass of the capsule.

Characteristics of the Stiffened Capsules

Preferably, the stiffened envelope of the capsules according to the invention has a thickness comprised from 10 μm to 1,000 μm, preferably from 1 μm to 1,000 μm, and advantageously from 20 μm to 500 μm.

The capsules according to the invention generally have a volume ratio between the core and the stiffened envelope of more than 2, and preferably less than 50.

According to a particular embodiment, the capsules according to the invention generally have a volume ratio between the core and the stiffened envelope comprised between 5 and 10.

The capsules according to the invention, provided with or without any gelled external envelope, generally have an average size comprised from 100 μm to 6 mm, preferably from 100 μm to 500 μm.

For a use of the capsules in a cell culture or in biology generally, an advantage size of the capsules is typically located from 100 μm to 500 μm.

For a use of the capsules in detergents, lubrication, in the cosmetic or food sector, an advantageous size of the capsules is typically located from 100 μm to 6 mm, more particularly from 100 μm to 2 mm.

Figure 2:
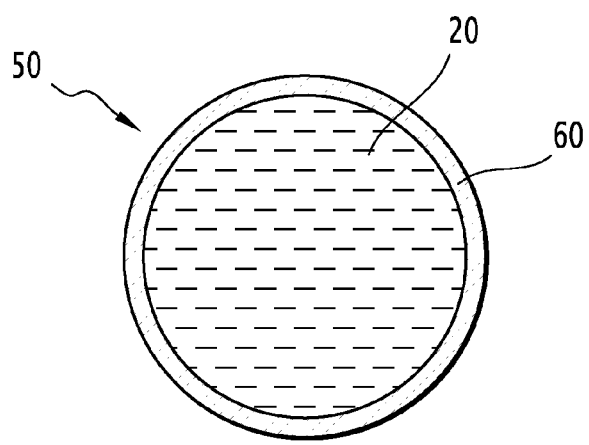

The invention will be better understood upon reading the following, only given as an example, and made with reference to the appended drawings, wherein:

FIG. 1 is a large scale view, in a section along a middle vertical plane of a gelled and stiffened capsule according to the invention; and FIG. 2 is a large scale view, in a section along a middle vertical plane of a stiffened capsule according to the invention.

A capsule 10 according to the invention comprises a liquid core 20, a stiffened intermediate envelope 30 and a gelled external envelope 40.

A capsule 50 according to the invention comprises a liquid core 20 and a stiffened envelope 60 encapsulating the whole of the outer surface area of the liquid core.

EXAMPLES

Experimental Device

The methods for preparing capsules is based on concentric co-extrusion of compositions via a three envelope device for forming multi-component drops.

A first composition (C1) circulating in a first compartment of a triple envelope forms the first flow.

A second composition (C2) circulating in a second compartment of the triple envelope forms the second flow.

A third composition (C3) circulating in a third compartment of the triple envelope forms the third flow.

Formation of Gelled and Stiffened Capsules

At the exit of the triple case, a multi-component drop is then formed, the first flow forming the liquid core, the second flow forming the liquid intermediate envelope and the third flow forming the liquid external envelope of the multi-component drop.

The size of the liquid core, the thickness of the intermediate envelope and of the external envelope of the form of the capsules are controlled by using several independent pusher syringes, adjusting the injection flow rates of the different compositions C1, C2 and C3.

The flow rate Q1 of composition C1 is adjusted to 10 ml/h.

The flow rate Q2 of the composition C2 is adjusted to 1 ml/h.

The flow rate Q3 of the composition C3 is adjusted to 1 ml/h and may be reduced down to 0.01 ml/h.

Each multi-component drop detaches itself from the triple envelope and falls in a volume of air, before being immersed in a gelling solution of calcium lactate concentrated to 1M.

Once the external envelope is gelled, the formed gelled capsules are rinsed in a rinsing solution based on water, and are then immersed in a stiffening bath.

Formation of Stiffened Capsules

The thereby formed gelled and stiffened capsules are then immersed in a depolarization solution of citrate concentrated to 10%.

Once the external envelope is depolymerized and removed, the obtained stiffened capsules are rinsed in a rinsing solution based on water and stored in a storage solution based on water.

Example 1

The composition C1 is an aqueous solution of an amaranth dye at 1 mM.

The composition C2 is an aqueous dispersion of natural latex (chemical name cis-1,4-polyisoprene, from the family of dienes, an example of commercial natural latex: natural rubber grade TSR, SRM, SIR, STR, SVR, ADS, RSS, Crepes, DPNR, from Astlett Rubber Inc.) diluted down to a mass fraction of particles of polymers from 20% to 40% based on the total mass of the natural latex dispersion, also comprising 1% by mass of a surfactant of the ionic or non-ionic type depending on the grade.

In this example, the mass fraction of particles of polymers is set to 30% (the latex dispersion is titrated by gravimetry after washing by centrifugation) and the SDS (sodium dodecylsulfate) surfactant is used.

The composition C3 is an aqueous solution having a mass percentage of sodium alginate of 2.0% and a mass percentage of SDS of 0.1%.

The obtained capsules, with a standard diameter of a few mm, are maintained in the gelling solution of calcium ions for one minute and are then rinsed with distilled water. They are then stored in an isotonic solution with the internal solution. Dual coacervation is thereby obtained by permeation of the calcium ions through the gelled alginate envelope. The capsules may then be incubated for 10 minutes in a 10% citrate solution in order to dissolve the outer membrane of hydrogel alginate. Capsules are thereby obtained having an outer envelope of stiffened natural latex.

Example 2

Example 2 is made under the same conditions as Example 1, except that the composition C2 further comprises carbon black "CB: carbon black". To do this, a CB solution is prepared (from the carbon black N234 from CABOT Corporation) in the presence of 2% SDS surfactant, the mass fraction of particles of polymers being always comprised between 20% and 40% based on the total mass of the natural latex dispersion, the CB fraction being comprised from 1% to 15%.

For this example, the mass fraction of particles of polymers is set to 30% and the CB mass fraction to 5% based on total mass of the composition C2.

After gelling of the alginate envelope, the capsules are incubated in distilled water for about 20 minutes. The surfactant diffuses towards the outside of the capsules through the alginate envelope and causes coacervation of the mixed natural latex/CB mixture, giving rise to a stiffened envelope of reinforced rubber.

Example 3

Example 3 is made under the same conditions as Example 1, except that the composition C2 further comprises colloidal silica with an average diameter of 100 nm (Aerosil from Degussa, Ludox from Sigma), according to a mass fraction from 1% to 15% based on the total mass of the composition C2.

For this example, the mass fraction of particles of polymers is set to 30% and the mass fraction of colloidal silica to 5% based on a total mass of the composition C2.

Capsules are thereby obtained including a stiffened envelope of reinforced rubber.

The capsules prepared according to the invention are easy to form, they have a resistant envelope of small thickness which gives the possibility of ensuring efficient disintegration of the capsule when the liquid contained in the capsule has to be released.

The invention claimed is:
1. A method for preparing capsules, each capsule comprising a liquid core and a stiffened intermediate envelope totally encapsulating at its periphery the liquid core, said method comprising the following steps of:
    (A) forming a multi-component liquid drop comprising:
        (1) a liquid core,
        (2) a liquid intermediate envelope formed with an intermediate composition comprising at least one first reagent R1, totally encapsulating at its periphery the liquid core, and
        (3) a liquid external envelope formed with an external aqueous composition, different from the intermediate composition, said composition comprising at least one polyelectrolyte different from the first reagent R1 and at least one surfactant, totally encapsulating at its periphery the intermediate envelope,
    (B) gelling by immersion of said multi-component liquid drop in a gelling solution containing a reagent able to gel the polyelectrolyte of the liquid external envelope, in order to obtain a gelled capsule comprising a gelled external envelope,
    (C) stiffening the first reagent R1 of the liquid intermediate envelope of the gelled capsule comprising a gelled external envelope obtained in (B), in order to obtain a gelled and stiffened capsule comprising a stiffened intermediate envelope, and
    (D) recovering said gelled and stiffened capsules.
2. The method according to claim 1, wherein the polyelectrolyte of the external composition is selected from polyelectrolytes which react to multivalent ions.
3. The method according to claim 2, wherein the polyelectrolyte is a sodium alginate.
4. The method according to claim 1, wherein the stiffening step is carried out by coacervation of the first reagent R1 of the liquid intermediate envelope.
5. The method according to claim 4, wherein the stiffening step is carried out by coacervation of the first reagent R1 caused by a variation of the temperature, of the pH, or by electromagnetic radiation.
6. The method according to claim 4, wherein the stiffening step is carried out by coacervation of the first reagent R1 with a multivalent cation.
7. The method according to claim 4, wherein the stiffening step is carried out by coacervation of the first reagent R1 with a second reagent R2, different from the first reagent R1.
8. The method according to claim 7, wherein the first reagent R1 is a hydrophilic anionic polymer and the second reagent R2 is a hydrophilic cationic polymer.
9. The method according to claim 7, wherein the first reagent R1 is a hydrophilic cationic polymer and the second reagent R2 is a hydrophilic anionic polymer.
10. The method according to claim 7, wherein the first reagent is a lipophilic cationic polymer and the second reagent R2 is a hydrophilic anionic polymer.
11. The method according to claim 4, wherein the first reagent R1 is in the form of latex of polymers.
12. The method according to claim 1, further comprising after the stiffening step, a step for depolymerizing the polyelectrolytes in the gelled state of the gelled external envelope, in order to remove the gelled external envelope.

* * * * *